(12) United States Patent
Goldfarb et al.

(10) Patent No.: US 10,952,877 B2
(45) Date of Patent: *Mar. 23, 2021

(54) COORDINATED CONTROL FOR AN ARM PROSTHESIS

(71) Applicant: VANDERBILT UNIVERSITY, Nashville, TN (US)

(72) Inventors: Michael I. Goldfarb, Franklin, TN (US); Nasser Alshammary, Nashville, TN (US); Daniel Bennett, Nashville, TN (US); Skyler Dalley, Shaker Hts., OH (US)

(73) Assignee: Vanderbilt University, Nashville, TN (US)

(*) Notice: Subject to any disclaimer, the term of this patent is extended or adjusted under 35 U.S.C. 154(b) by 74 days.

This patent is subject to a terminal disclaimer.

(21) Appl. No.: 16/155,150

(22) Filed: Oct. 9, 2018

(65) Prior Publication Data

US 2019/0105185 A1 Apr. 11, 2019

Related U.S. Application Data

(63) Continuation of application No. 14/929,779, filed on Nov. 2, 2015, now Pat. No. 10,092,423, which is a
(Continued)

(51) Int. Cl.
*A61F 2/58* (2006.01)
*A61F 2/72* (2006.01)
(Continued)

(52) U.S. Cl.
CPC .................. *A61F 2/72* (2013.01); *A61F 2/58* (2013.01); *A61F 2/582* (2013.01); *A61F 2/583* (2013.01);
(Continued)

(58) Field of Classification Search
CPC .......................... A61F 2/582; A61F 2002/546
See application file for complete search history.

(56) References Cited

U.S. PATENT DOCUMENTS

| | | | | |
|---|---|---|---|---|
| 10,092,423 | B2 * | 10/2018 | Goldfarb | ................... A61F 2/58 |
| 2011/0264238 | A1 * | 10/2011 | van der Merwe | ...... A61F 2/585 623/24 |
| 2014/0188251 | A1 | 7/2014 | Mosler | |

FOREIGN PATENT DOCUMENTS

| | | |
|---|---|---|
| CA | 2761809 A1 | 10/2010 |
| WO | WO 01/143669 A1 | 6/2001 |

(Continued)

OTHER PUBLICATIONS

Notice of Opposition to European Patent No. 299159281, dated Apr. 19, 2018; pp. 1-17.
(Continued)

*Primary Examiner* — David H Willse
(74) *Attorney, Agent, or Firm* — Nixon Peabody LLP (57) ABSTRACT

A control method for an arm prosthesis having at least one powered joint and at least one inertial measurement sensor (IMS) includes determining a motion and an orientation of the arm prosthesis relative to the inertial reference frame based at least on an output of the IMS and generating control signals for the at least one powered joint based on the motion and the orientation of the prosthetic arm.

13 Claims, 5 Drawing Sheets

Related U.S. Application Data continuation of application No. PCT/US2014/036599, filed on May 2, 2014.

(60) Provisional application No. 61/818,596, filed on May 2, 2013.

(51) Int. Cl.
    *A61F 2/70*      (2006.01)
    *G05B 15/02*      (2006.01)
    *A61F 2/54*      (2006.01)
    *A61F 2/76*      (2006.01)

(52) U.S. Cl.
CPC .............. *A61F 2/585* (2013.01); *G05B 15/02* (2013.01); *A61F 2002/543* (2013.01); *A61F 2002/546* (2013.01); *A61F 2002/704* (2013.01); *A61F 2002/762* (2013.01); *A61F 2002/763* (2013.01); *A61F 2002/764* (2013.01); *A61F 2002/7625* (2013.01); *A61F 2002/7635* (2013.01)

(56) References Cited

FOREIGN PATENT DOCUMENTS

WO    WO 2010/120403 A2    10/2010
WO    WO 2013/010597 A1    1/2013

OTHER PUBLICATIONS

English Translation of Notice of Opposition to European Patent No. 299159281, dated Apr. 19, 2018; pp. 1-17.

Nasser A. Alshammary et al.; "Assessment of a Multigrasp Myoelectric Control Approach for use by Transhumeral Amputees"; 1 Page, Author Manuscript, Published in final edited form as: Conf. Proc. IEEE, Eng. Med. Biol. Soc. 2012; 2012: 968-971 (4 pages).

International Search Report and Written Opinion dated Sep. 12, 2014 in PCT/US2014/036599.

* cited by examiner

COORDINATED CONTROL FOR AN ARM PROSTHESIS

CROSS REFERENCE TO RELATED APPLICATIONS

This application is a continuation of and claims the priority to U.S. Non-Provisional application Ser. No. 14/929,779, filed Nov. 2, 2015, now U.S. Pat. No. 10,092, 423, and entitled "Coordinated Control for an Arm Prosthesis", which is a continuation of Application No. PCT/US2014/036599, filed May 2, 2014, and entitled "Coordinated Control for an Arm Prosthesis", which claims priority to and the benefit of U.S. Provisional Patent Application No. 61/818,596, filed May 2, 2013 and entitled "Coordinated Control for an Arm Prosthesis", the content of all of which are herein incorporated by reference in their entireties.

FIELD OF THE INVENTION

The present invention relates to control of arm prostheses, and more specifically to apparatus and methods for coordinating operation of joints in myoelectric arm prostheses.

BACKGROUND

In many conventional myoelectric arm prostheses with a powered elbow joint, the configuration of the powered elbow joint is typically controlled irrespective of the configuration of the shoulder joint, and the wrist joint is typically controlled irrespective of the configuration of the other major joints in the arm. Further, in such myoelectric arm prostheses, the configuration of each joint in the prosthetic arm is typically controlled in a sequential manner (i.e., one joint is moved at a time), until the arm is configured in a desired posture.

The reason that conventional myoelectric prostheses are typically configured in a sequential manner is that the at least one joint of the myoelectric arm prosthesis is typically controlled with input from a pair of electromyogram (EMG) measurements, each of which measures the electrical activity resulting from a muscle contraction in a pair of opposing muscles in the residual limb of the amputated arm. In the case of an above-elbow amputation, the EMG is typically measured from the biceps and triceps muscle groups. In the anatomical arm, the combination of the pair of measurements provides a single bidirectional control for flexing or extending a given joint. Although the biceps and triceps muscles no longer act to flex and extend an anatomical elbow joint in above-elbow amputees, filtered and rectified EMG measurements can provide a real-time electrical signal proportional to the strength of contraction of the respective muscles in the residual limb. In most myoelectric arm prostheses, this electrical signal drives an elbow motor control loop for the prosthesis, such that the angular velocity of the prosthetic elbow joint is proportional to the measured EMG, where EMG is measured from the biceps muscle group for flexion and EMG is measured from the triceps muscle group for extension. Therefore, the angular speed of the elbow joint is generally proportional to the strength of contraction. In the absence of muscle contraction, the elbow remains locked at its current position (i.e., the joints of a myoelectric prosthetic arm are normally-locked). This control method can be referred to as differential, velocity-based EMG control.

In the case of an arm prosthesis with powered elbow and wrist joints, coordinated control of these joints is typically not possible since only a single control signal (from the biceps and triceps) is available for controlling these multiple joints. As a result, the EMG control signal is typically switched between joints, resulting in the joints being controlled in a sequential fashion. For example, the EMG from biceps/triceps will first be used to move the prosthetic elbow joint. Thereafter, control may be switched to the wrist joint (typically by momentarily co-contracting both the biceps and triceps in unison, rather than using them in a differential sense) and the EMG from the biceps/triceps can adjust the angle of the wrist. A further momentary co-contraction will switch control to a prosthetic hand, such that the same EMG will open/close the hand. A subsequent momentary co-contraction will cycle EMG control back to the elbow joint. As such, the same agonist/antagonist muscle group (in this case biceps and triceps) provide myoelectric control of all of the joints and the hand of the prosthetic arm.

With respect to coordinated control of the powered elbow joint and the intact shoulder joint in an above-elbow prosthesis, the powered elbow unit could be moved in concert with the shoulder, but not without great difficulty. In particular, since substantial portions of both the biceps and triceps extend over the shoulder joint (i.e., both are two-joint muscle groups), movement of the intact shoulder also produces myoelectric signals in the biceps and triceps. Therefore it is difficult, if not impossible, particularly without elbow proprioception, for the amputee to provide EMG signals to control the prosthetic elbow joint that are decoupled from EMG signals generated during use of the intact shoulder joint. As a result, the amputee typically resorts to the independent, sequential configuring of the shoulder and elbow joints, which removes the interference that shoulder movement presents in the biceps and triceps EMG signals. Therefore, above-elbow amputees are typically forced to move all joints of the arm in a sequential manner.

SUMMARY

Embodiments of the invention concern systems and methods for controlling the operation of arm prostheses. In particular, the present technology is directed to systems and methods for the control of an arm prosthesis, where the prosthesis consists of at least one powered joint, and further comprises at least one inertial measurement sensor (IMS), where the inertial measurement sensor is used to measure the motion of the prosthetic limb, and by association the residual limb, relative to the inertial reference frame, and wherein the motion of the residual limb is used as a control input for controlling the movement of the at least one powered joint.

In particular configurations, the at least one powered joint is an elbow joint and the residual limb is the upper arm, where the inertial measurement sensor measures the motion of the upper arm, and where the angular movement of the elbow joint is controlled in relation to the measured motion of the upper arm. The inertial measurement of the upper arm motion can be a measurement of upper arm spatial orientation and/or angular velocity with respect to an inertial reference frame.

In particular configurations, the elbow joint angular movement is controlled as a function of the upper arm spatial orientation, such that the elbow joint moves in extension when the upper arm orientation indicates that the elbow is moving away from the body, and such that the elbow joint moves in flexion when the upper arm orientation indicates that the elbow is moving closer to or toward the body. The movement of the elbow toward or away from the body can be indicated by the radial distance of the elbow from the body centerline. Alternatively, the movement of the elbow toward or away from the body can be indicated by the distance of the elbow joint from the body center projected onto a preselected plane relative to the body of the wearer, such as the sagittal plane, frontal plane, or mid-sagittal plane. Additionally, the movement of the elbow toward or away from the body can be indicated by the distance of the elbow joint from the body center projected onto a preselected plane relative to the orientation of the axis of rotation of the elbow joint.

In some configurations, an elbow joint angular velocity can be caused by an instantaneous linear velocity of the elbow joint in a direction orthogonal to both the elbow axis of rotation and the long axis of the upper arm. Accordingly, the elbow joint angle can move in flexion when the instantaneous linear velocity is toward the body centerline and move in extension when the velocity is away from the body centerline.

In still other configurations, an angular velocity of the elbow joint can be caused by an angular velocity of the upper arm with respect to an inertial reference frame. The angular velocity of the upper arm can be the component of angular velocity along the rotational axis of the elbow joint. Alternatively, the angular velocity of the upper arm can be the vector sum of angular velocity components in the plane orthogonal to the long axis of the upper arm. In some cases, the angle of shoulder internal/external rotation is used to modulate a gain between elbow joint angular velocity and upper arm angular velocity.

In particular configurations, the elbow joint can be controlled such that the orientation of the forearm with respect to the inertial reference frame remains invariant for upper arm movement in the plane orthogonal to the axis of the elbow joint.

In the various configurations, electromyogram (EMG) control of the elbow joint can be combined with IMS control of the elbow joint. In some cases, the EMG from the upper arm can be combined with measured orientation of the upper arm from the IMS to cause movement of the elbow joint. Further, a differential EMG elbow angular velocity control can be superimposed onto the IMS control.

Additionally, a sustained co-contraction as indicated by EMG can be used to prevent elbow joint movement or attenuate elbow joint movement in relation to the strength of co-contraction.

In some configurations, an angular velocity of the upper arm can be used to prevent differential EMG control of elbow joint movement. Alternatively, absence of angular velocity of the upper arm can switch control of elbow joint motion to differential EMG control.

In some configurations, the prosthesis can be switched between the coordinated control mode and a sequential control mode. This switching can be based on at least an EMG or an IMS event.

In some configurations, the at least one powered joint can include a powered wrist joint. The powered wrist joint can be controlled such that the orientation of the hand remains invariant relative to the inertial reference frame. Further, a co-contraction of muscles in the residual limb can be used to select the coordinated wrist control mode.

DETAILED DESCRIPTION

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

This present technology is directed to a control methodology that enables above-elbow amputees with myoelectric prostheses to effect coordinated, simultaneous movements of their anatomical shoulder joints and prosthetic elbow joints. In subjects with a healthy or intact arm, the major joints (i.e., shoulder, elbow, and possibly wrist) are typically controlled simultaneously in order to achieve a desired configuration of the arm. Configuring all joints simultaneously provides a number of important advantages relative to configuring them sequentially. The most obvious is that sequential configuration requires more time than simultaneous configuration of the joints, assuming the time required to configure each joint is essentially invariant. Therefore, obtaining a desired posture with simultaneous configuration of the joints enables a faster movement of the arm. Perhaps more significantly, a user is often interested in following a given path with his or her hand, rather than simply achieving a given final position of the hand. For example, in a reaching motion, or in opening a door or a drawer, the desired movement involves configuring the arm such that the hand follows a path or a trajectory, rather than simply obtaining a single pose with the arm.

As is known in the study of robot manipulators, the ability to move the endpoint (in this case, the hand) of a multi joint manipulator (in this case, the arm) along an arbitrary path requires the simultaneous movement of multiple joints in the arm. For example, for a two-joint manipulator consisting of a one-axis shoulder and one-axis elbow joint, moving the endpoint (i.e., hand) in a straight line path requires the simultaneous movement of both the shoulder and elbow joints. If the joints are moved sequentially, the path is instead constrained to move along one of two arc-shaped paths (an arc with a center located either at the shoulder or elbow, depending on which joint is being sequentially moved). Thus, the inability to configure multiple joints in a serial manipulator (i.e., arm) simultaneously increases the time to achieve a given configuration, and restricts severely the ability to move the hand along a generalizable path or trajectory.

In view of the limitations of existing myoelectric prostheses, the present technology is directed to a control methodology that enables above-elbow amputees with myoelectric prostheses to effect coordinated, simultaneous movements of their anatomical shoulder joints and prosthetic elbow joints. Although the various embodiments will be described primarily with respect to coordinating the control of a prosthetic elbow joint in an above-elbow myoelectric arm with the movement of the intact shoulder joint, the methodology of the present technology is also more broadly applicable to above-elbow and below-elbow myoelectric arms with wrist joints.

Figure 1:
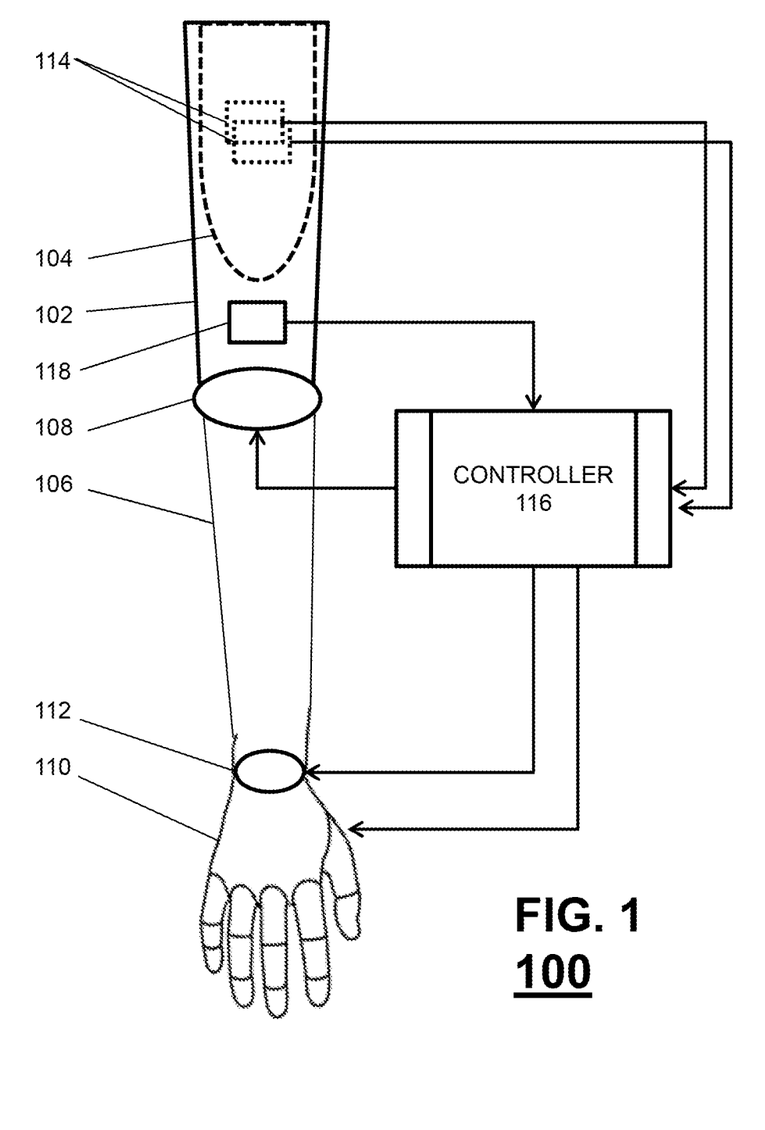
FIG. 1 shows a schematic illustration of a prosthetic arm in accordance with the present technology.

Turning first to FIG. 1, there is shown an above-elbow myoelectric arm prosthesis 100 in accordance with the present technology. As shown in FIG. 1, the arm prosthesis 100 includes an upper arm portion 102, with a socket 104 for receiving a residual limb, a forearm portion 106, and a powered elbow joint 108 rotatably coupling the forearm portion 106 and the upper arm portion 102. The powered elbow joint 108 can be configured to provide extension or flexion of the arm prosthesis 100.

A distal end of the forearm portion 106, the arm prosthesis 100 can include a hand portion 110. The hand portion 110 can include one or more powered joints. Further, although the hand portion 110 is shown as a hand-type terminal device, the hand portion 110 can be a non-anthropomorphic terminal device, such as a hook-type device.

The hand portion 110 can be coupled via a wrist joint 112. In some configurations, the wrist joint 112 can be passive. However, in other configurations, the wrist joint 112 can be powered as well and provide motion along one or more degrees of freedom.

As noted above, the arm prosthesis 100 can be controlled myoelectrically. Accordingly, the arm can include EMG sensors 114 for detecting EMG signals generated by different muscle groups. Additionally, the arm prosthesis 100 can include a controller 116 for receiving the EMG signals from EMG sensors 114 and for generating control signals for the elbow joint 108 and, if needed, for a wrist joint 112 and hand 110.

In addition to the above-mentioned components, which provide basic myoelectric operation of arm prosthesis 100, as previously described, the arm prosthesis 100 can also include components to support the coordinated control of joints in accordance with the present technology.

In particular, the arm prosthesis can include an inertial measurement unit (IMS) 118 that can be used to compute in real-time the motion (relative to an inertial reference frame) of the upper arm portion 102, and therefore estimate the motion of wearer's residual limb. As used herein, the motion information obtained based on the IMS 118 can encompass one or more of displacement or position, direction, velocity, acceleration, and time. In a particular embodiment, the IMS is located on the forearm portion 106 of arm prosthesis 100, although it can be located on any part of arm prosthesis 100. In some embodiments, IMS 118 can comprise a 3-axis gyroscope from which an angular velocity can be computed in multiple directions or axes. In other embodiments, the IMS 118 can comprise a single-axis gyroscope from which the angular velocity can be along a single direction or axis. In still other embodiments, IMS 118 can comprise accelerometers, gyroscopes, and potentially magnetometers. For example, in one particular embodiment, IMS 118 is a nine-axis IMS that includes a 3-axis accelerometer, a 3-axis gyroscope, and a 3-axis magnetometer. The data from these elements can then be used by controller 116 to compute the 3-dimensional orientation of the upper arm portion 102 and thus estimate the 3-dimensional orientation of a residual limb in socket 104 in real-time. The computation for a nine-axis IMS, such as IMS 118, is described below.

In general, a 3-axis magnetometer provides a low-frequency measure of the direction of the magnetic north vector (relative to the Earth, or inertial-reference frame). The 3-axis accelerometer provides a low-frequency measure of the direction of the gravity vector (relative to the Earth frame) and the 3-axis gyroscope provides angular velocities about each of the IMS's principal axes. The measured orientations of the magnetic north and gravity vectors can be used to compute an orthonormal basis of vectors ($u_1$, $u_2$, $u_3$) of the reference frame for the IMU. This orthonormal basis represents the three-dimensional orientation of the IMU relative to the inertial reference frame (IRF), and can be computed from:

$$u_1 = g \tag{1}$$

$$u_2 = g \times m \tag{2}$$

$$u_3 = u_1 \times u_2 \tag{3}$$

where g is the measured gravity vector and m is the measured magnetic north vector.

Concatenating this set of vectors forms a rotation matrix which represents the steady state orientation of the IMS. Since the accelerometer and magnetometer generally provide low-frequency (essentially steady-state) measurements, this information can be combined with the measured angular velocity from the gyroscope to provide high-frequency measurement.

Specifically, the gyroscope provides angular velocities about each principal axis of the IMS, which are integrated to calculate an estimation of the angular position of the IMS. Since the integration may result in drift over a prolonged period, only the high-frequency information from the gyroscope is used. By using a complementary filter approach to combine the low-frequency information from the magnetometer and accelerometer with the high-frequency information from the gyroscope, the three sensing modalities of the 9-axis IMS can provide a single rotation matrix with good accuracy and dynamic response, thus providing a real-time measurement of IMS orientation.

Figure 2:
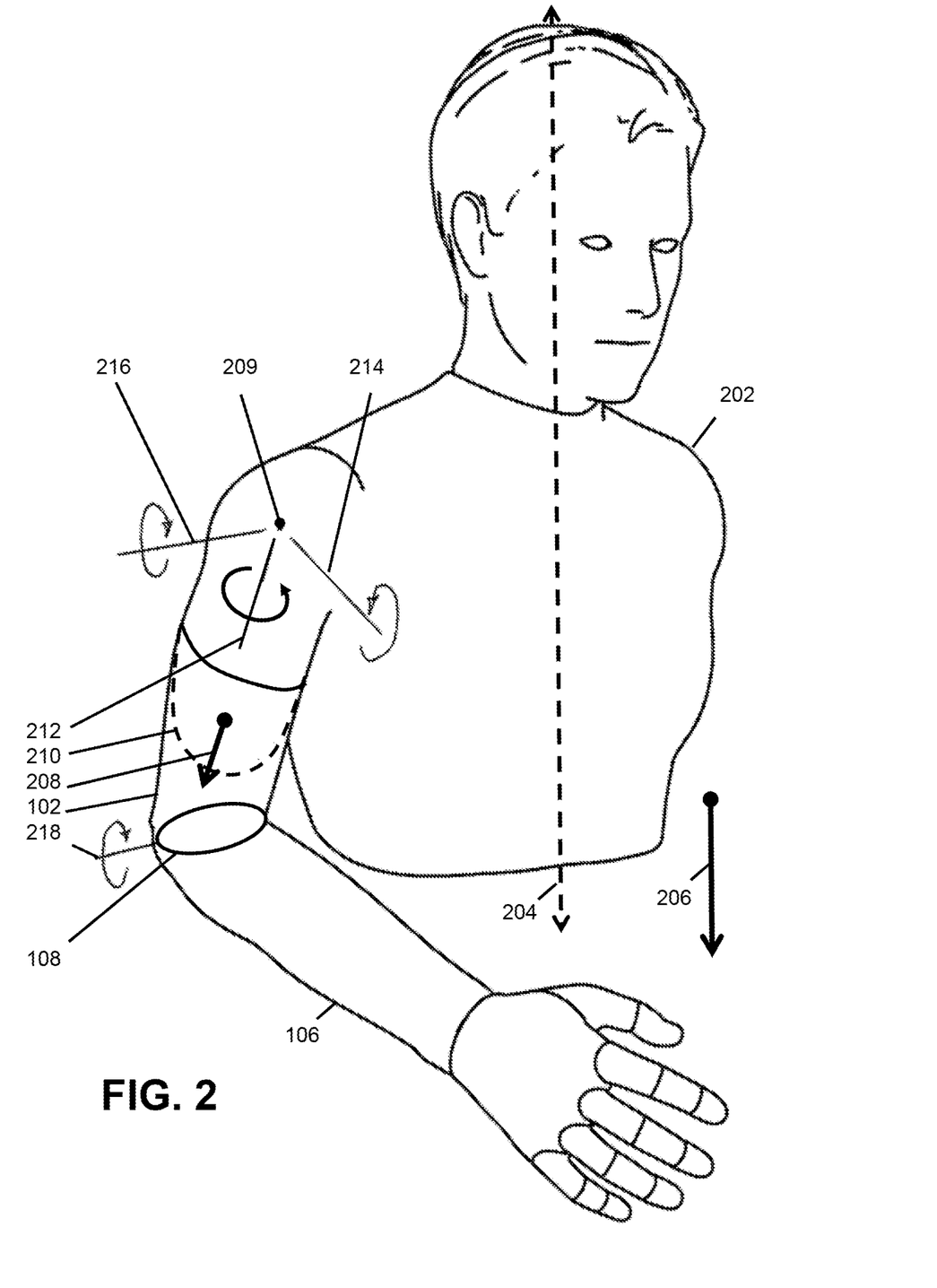
FIGS. 2 and 3 illustrates a user with the prosthetic arm of FIG. 1.

Referring back to FIG. 1, the IMS 118 is shown as being located on upper arm portion 102 of arm prosthesis 100. However, since all configuration angles within arm prosthesis 100 are known, the motion of upper arm portion 102 can be computed, and that of residual arm as well, regardless of the location of the IMS 118 in arm prosthesis 100. Thus, the IMS 118 can be located anywhere on arm prosthesis 100 in the various embodiments. For example, if the IMS 118 is situated on the forearm of the arm prosthesis, and if the elbow joint angle is measured (e.g., with an angular position sensor such as a rotary encoder), the orientation and motion of the wearer's upper arm (i.e., residual limb) can be determined relative to the inertial reference frame. Using the orientation or angular velocity information from the IMS 118, the controller 116 can then be used to coordinate motion of the powered joints in arm prosthesis 100 with that of the intact shoulder joint, as illustrated in FIG. 2. In particular, assuming the upper body 202 (i.e., torso) of the user remains relatively stationary in or near a known configuration (e.g., a center line 204 of the upper body is approximately parallel to a gravity vector 206), the configuration or movement of the shoulder joint 209 can also be estimated by the controller 116 in real-time based on the orientation or angular velocity information 208 obtained using IMS 118 for the residual limb 210. In particular, the IMS information 208 can be utilized by the controller 116 to extrapolate shoulder movement in rotation 212, abduction/adduction 214, and/or flexion/extension. Based on this estimate of shoulder motion and/or configuration, the rotation 218 of the powered elbow joint 108 can be specified by controller 116 such that it moves in a coordinated fashion with the shoulder joint. Thus, the controller 116 can be configured to provide movement coordination between the powered elbow joint 108 and the (intact) shoulder joint 209. This coordinated movement can be independent of the EMG measurements from the residual limb, or can be modulated by or coordinated with the EMG input patterns to modify the pattern of coordination between the elbow and shoulder joints.

Figure 3:
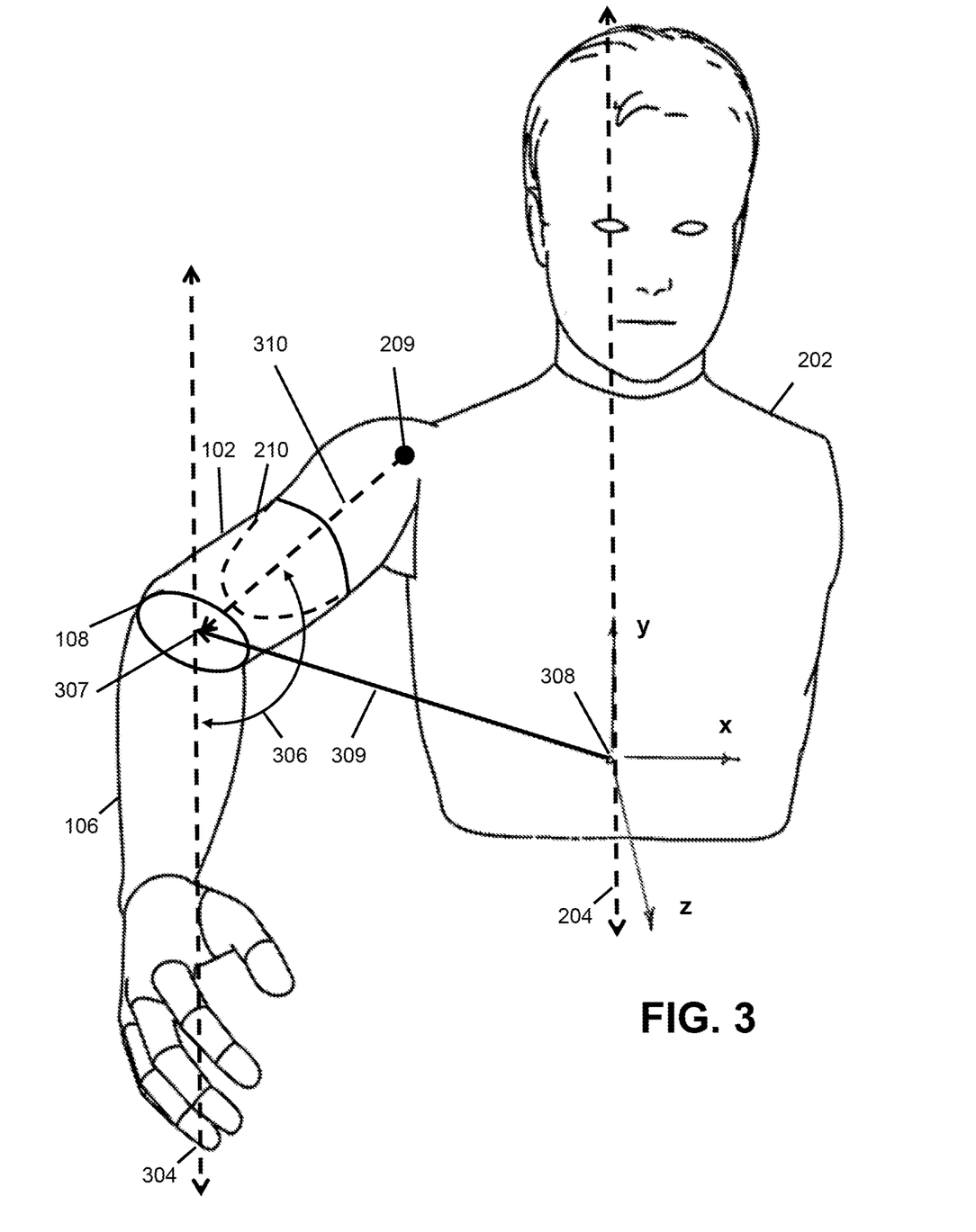

In one particular embodiment, the controller 116 can be configured to operate the arm prosthesis 100 in a reaching mode. In the reaching mode, the powered elbow joint 108 is flexed or extended in relation to the estimated distance 309 between a location 307 of the powered elbow 108 and approximate centerline 204 of the body 202. In the reaching mode, it is also important to distinguish between the elbow joint location 307, which is a function of the upper arm orientation (and therefore a function of shoulder angle), and the elbow joint angular position 306, which is the angle formed between the forearm portion 106 and upper arm portion 102. The powered elbow joint location 307 can be identified by three Cartesian coordinates with respect to a reference 308 along centerline 204, while the elbow joint angle 306 (or elbow angle) is a scalar (since the powered elbow joint 108 is assumed to be a hinge, and thus has a single degree of freedom). The elbow joint angle 306 is described anatomically as elbow flexion and extension, where flexion decreases the angle between the forearm portion 106 and upper arm portion 102, and extension increases it. The shoulder joint 209 is assumed to be a ball joint, and therefore has three degrees of freedom, described by flexion/extension, abduction/adduction, and internal/external rotation (as shown in FIG. 2).

The location 307 of the powered elbow joint 108 relative to the body centerline 204 can be regarded as the elbow position in the Cartesian frame, while the angles of the elbow joint 108 and the shoulder joint 209 can be regarded as the elbow and shoulder joint angles in the configuration frame. Note that shoulder flexion/extension and abduction/adduction in the configuration frame generally result in elbow movement in the Cartesian frame, while shoulder internal/external rotation in the configuration frame results in re-orientation of the elbow joint in the Cartesian frame, but not elbow joint movement through the Cartesian frame.

In the reaching mode, if the shoulder joint 209 moves the powered elbow joint 108 away from the body 202 (in the Cartesian frame), the controller 116 can cause the powered elbow joint 108 to be extended (in the configuration frame) in relation to the linear distance between the elbow and body centerline. If the shoulder joint 209 moves the powered elbow joint 108 toward the body 202, the controller 116 configures the powered elbow joint 108 to be flexed in relation to the distance between the powered elbow joint 108 and the centerline 204. The estimated distance 309 can then be computed by the controller 116 as a function of the orientation of the upper arm portion 102 (which can be used to approximate shoulder configuration) and the known length 310 from the intact shoulder joint 209 to the powered elbow joint 108. Alternatively, an alternate estimation is to use only the spatial orientation of the upper arm portion 102 to estimate the distance between the powered elbow joint 108 and centerline 204. In this approach, the elbow angular velocity is essentially proportional to the component of velocity with which the powered elbow joint is moving away from or towards the centerline 204 (where away from results in an extensive angular velocity and towards results in a flexive angular velocity).

The operation of the reaching mode can be further refined by using the orientation of the powered elbow joint 108 in relation to the shoulder joint 209 in order to further specify the action for the powered elbow joint 108. In particular, the movement of the powered elbow joint 108 can occur in relation to the projection of shoulder joint movement onto the plane orthogonal to the elbow joint axis of rotation (which is the plane containing the forearm portion 106 and the upper arm portion 102). In this manner, only shoulder joint movement in substantially the same plane as potential elbow joint movement will cause the controller 116 to generate coordinated movement in the powered elbow joint 108. Therefore, detecting reaching with the shoulder joint 209 in a plane substantially orthogonal to the current axis of elbow joint rotation 218 will cause the controller 116 to generate simultaneous coordinated reaching with the powered elbow joint 108, while reaching with the shoulder joint 209 in a substantially different plane will not cause the controller 116 to generate a simultaneous coordinated movement of the powered elbow joint 108. In this manner, the user can control whether or not coordinated reaching, using the powered elbow joint 108, will occur by orienting the shoulder appropriately. This approach is essentially the same as using the rotation about the long axis of the humerus bone (i.e., internal/external rotation 212 of the shoulder) to control the extent to which elbow flexion/extension is linked to elbow movement in the inertial reference frame.

In some configurations, the controller 116 can be configured such that the coordinated action between the shoulder joint 209 and powered elbow joint 108 only occurs in a preselected plane. For example, the controller 116 can be configured to provide coordinated action only when the arm prosthesis 100 is oriented essentially in the sagittal plane. Alternatively, the controller 116 can be configured to coordinate action only when the arm prosthesis 100 is oriented essentially in the frontal or mid-sagittal planes. In all cases, the controller 116 utilizes the measured movement of the upper arm 102 to generate flexion or extension of the powered elbow joint 108, where the extra degrees-of-freedom in the shoulder joint 209 (three in the shoulder relative to one in the elbow) are used to modulate the relationship between movement of the upper arm portion 102 and movement of the powered elbow joint 108. In addition to using the IMS 118 to command flexion and extension of the powered elbow joint 108, the controller 116 can also be configured to combine an IMS coordinated control approach with EMG measurement from the upper arm (i.e., from the biceps and triceps muscle groups) to modify the IMS coordinated control approach. In one embodiment, standard EMG control, in which the differential amplitude of the EMG signals is used to command an angular velocity of the powered elbow joint 108, can be superimposed on the IMS coordinated control approach, which has the effect of moderating or modifying the coordinated control action by superimposing an elbow angular velocity command from the EMG onto the elbow angular velocity command from the IMS.

In another embodiment of the controller 116, a sustained co-contraction of the biceps and triceps musculature (as measured via EMG sensors 114) can be used by the controller 116 to lock out the influence of the IMS 118, such that movement of the upper arm portion 102 does not affect movement of the powered elbow joint 108 while the user is co-contracting musculature in the residual limb. Note that this approach has a biological analog, since a healthy individual will generally co-contract agonist/antagonist musculature in order to prevent a joint from moving.

In a variation of this approach, the strength of co-contraction (as measured via EMG sensor 114) can be used by the controller 116 to inversely modulate the gain of the previously described IMS coordinated control approach (e.g., modulate the gain relating the extension and flexion angular velocity of the powered elbow joint 108 to the component of linear velocity away from and toward, respectively, the body centerline 204). A strong co-contraction would essentially cause the controller 116 to zero the gain (i.e., lock the powered elbow joint 108, and decouple motion of the powered elbow joint 108 from motion in the shoulder joint 209), while a weak co-contraction would cause the controller 116 to slightly attenuate the gain (i.e., maintain but slightly lessen the coupling between motion in the shoulder joint and motion in the powered elbow joint 108).

In some embodiments, movement of the upper arm portion 102 (as detected by IMS 118) can be used by the controller 116 to effectively lock out differential (velocity-based) EMG control of the powered elbow joint 108. Additionally, the absence of motion in the shoulder joint 209 (and thus in upper arm portion 102) can be used by the controller 116 to enable standard EMG-based differential velocity control. Therefore, when the controller 116 detects that the shoulder joint 209 (and the upper arm portion 102) is moving, the powered elbow joint 108 is controlled using a IMS-based coordination controller (potentially modulated by EMG co-contraction), and when the shoulder joint 209 (and the upper arm portion 102) are not moving, the controller 116 reverts to the standard EMG-based differential velocity control.

With this control architecture implemented in controller 116, if the user co-contracts strongly while moving the upper arm portion 102, the IMS controller is locked out and the controller 116 essentially operates as a standard differential EMG velocity controller. By lessening the strength of the co-contraction during movement of the upper arm portion 102 (and the shoulder joint 209), the controller 116 complements the traditional (differential EMG) control method with the previously described IMS-based coordinated control approach. In this manner, the user can independently control movement of the powered elbow joint 108 when desired, and can alternatively leverage coordinated control of the shoulder joint 209 and powered elbow joint 108 movement when desired.

In a different embodiment, the controller 116 can be configured so that the coordination between the powered elbow joint 108 and shoulder 209 can be such that the forearm portion 106 remains at a fixed orientation relative to the inertial reference frame for shoulder movement in the plane orthogonal to the axis 218 of the powered elbow joint 108. For example, if the axis 218 of the powered elbow joint 108 is orthogonal to the vertical, then movement of the shoulder joint 209 is such that the upper arm portion 102 moves in the vertical plane will control the powered elbow joint 108 such that the forearm portion 106 remains at the same angle with respect to the vertical. If the axis 218 of the powered elbow joint 108 is orthogonal to the horizontal plane, movement of the shoulder that moves the upper arm in the horizontal plane will maintain the orientation of the forearm portion 106 relative to an inertial reference frame in the horizontal plane. When moved in a different plane, the projection of the angle of the forearm portion 106 with respect to the inertial reference frame onto the plane orthogonal to the axis 218 of the powered elbow joint 108 will remain invariant.

Further, in this embodiment, the prescribed angle at which the forearm portion 106 remains invariant with respect to the inertial reference frame can be adjusted by the controller 116 by using EMG input from the residual limb in a manner similar to the typical myoelectric control of the powered elbow joint 108. Thus, EMG control of the angle of the powered elbow joint 108 can be superimposed onto the coordinated control of the powered elbow joint 108, such that the movement of the powered elbow joint 108 is both a function of EMG and movement of the shoulder joint 209.

In all embodiments of the control methodology of the present technology, it may be useful for the controller 116 to be configured to allow the user to switch between a coordinated control mode and a strictly sequential control mode. In a preferred embodiment, the control approach will automatically switch into standard differential EMG velocity control in the absence of movement of shoulder joint 209 (as detected via IMS 118). In another embodiment, the user can switch between these modes by a co-contraction pulse of both the biceps and triceps muscles, which is a commonly used method for switching control between joints in a multi joint arm or for selecting various modes of operation. The switching signal can be a single co-contraction or a pattern of multiple co-contractions.

Alternatively, the user can switch between modes via the IMS 118. In particular, the user can perform a specific movement and the IMS 118 then generates a set of signals that causes the controller 116 to switch between modes. For example, the user can perform a sudden abduction of the shoulder joint 209, which can be used to indicate that the user would like to switch between the coordinated and sequential control modes. Alternatively, information from the two sensors can be combined, such that switching is indicated by a co-contraction (as measured via EMG 114) and simultaneous sudden movement of the shoulder joint (as measured by the IMS 118).

In some embodiments, the arm prosthesis 100 can contain a powered wrist joint 112, as described above with respect to FIG. 1. In such embodiments, the IMS 118 can be used to determine the orientation of the prosthetic hand 110 relative to the inertial reference frame. For example, as noted above, the configuration of the arm prosthesis 100 is generally known and the orientation of its various components can therefore be determined based off a single IMS. However, the present technology is not limited in this regard and an IMS can be additionally provided for prosthetic hand 110.

When switched into a wrist control mode, the joints of the arm prosthesis 100 can be coordinated with the movement of the shoulder joint 209 to maintain the prosthetic hand 110 in a prescribed orientation. For example, when the powered elbow joint 108 is fully extended, the prosthetic hand 110 can be rotated about the axis of the arm prosthesis 100 either by pronation supination of the wrist or by internal and external rotation of the shoulder. In this coordinated control mode, if the shoulder joint 209 were internally or externally rotated, the powered wrist joint 112 would provide an equal and opposite wrist pronation or supination, such that the hand would not rotate relative to the inertial reference frame. Flexion and extension or ulnar and radial deviation can be controlled similarly. This mode of operation can be switched by an EMG or IMS event, or some combination thereof. In a preferred embodiment, a sustained EMG co-contraction would cause the wrist to operate in this mode for the duration of the sustained co-contraction.

Figure 4:
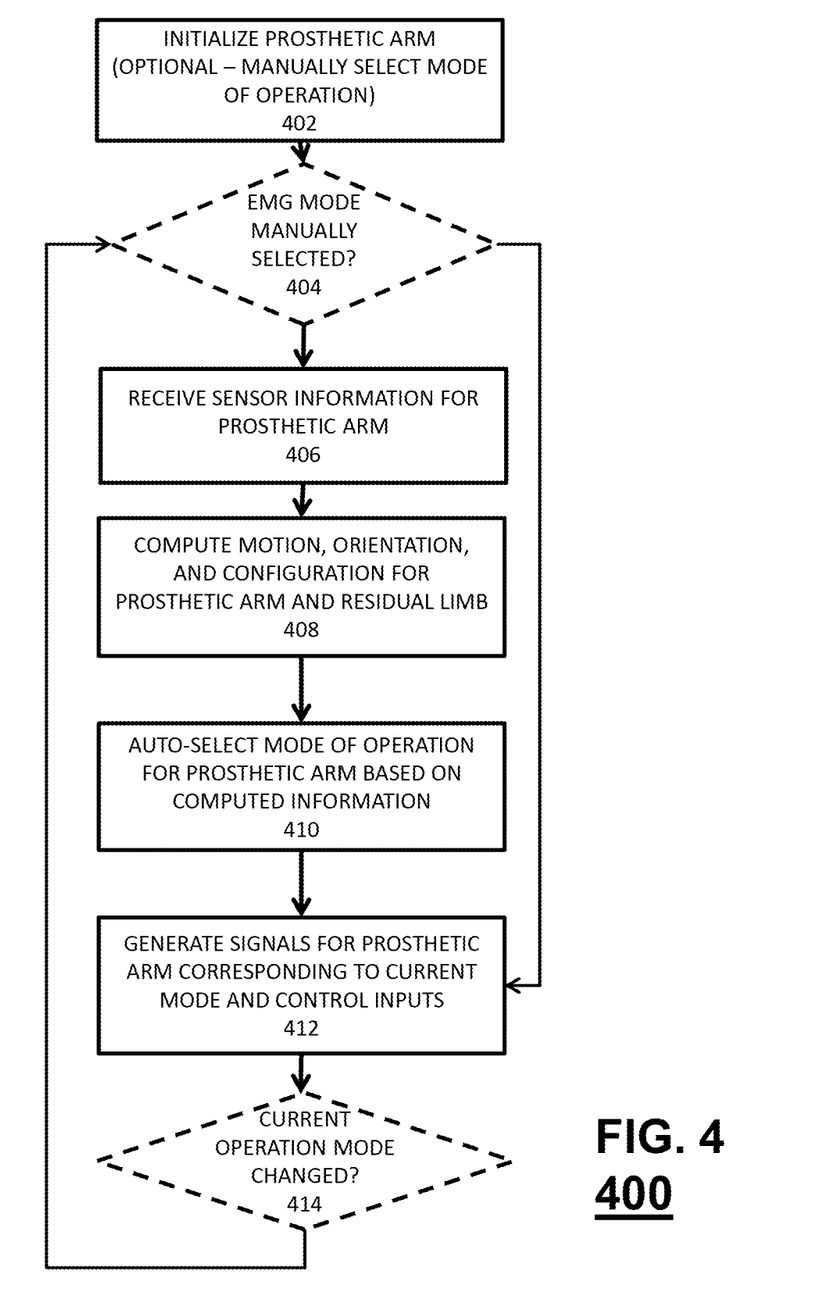
FIG. 4 shows a flowchart of steps in an exemplary method according to the present technology.

Now turning to FIG. 4, there is shown a flowchart of steps in an exemplary method 400 for coordinated control of a prosthetic arm in accordance with the present technology. The method begins at step 402. At step 402, the prosthetic arm prosthesis 100 can be initialized. In some configurations, this merely involves the powering the controller 116 in arm prosthesis 100. Optionally, this can involve manually selecting a mode of operation. That is, a user could select to operate the arm prosthesis 100 in a conventional EMG mode or allow the arm prosthesis 100 to auto-select between the conventional EMG mode and a coordinated control mode based on motion, orientation, and configuration information for the arm prosthesis 100, as described above. In such configurations, a mechanical switch can be provided on arm prosthesis 100, the mode can be selected at step 404 based on co-contractions detected by EMG sensors 114, or some other methodology can be provided for setting this operation mode at step 404.

In the case of manual mode selection, the method 400 can thereafter proceed to step 404. At step 404 it is determined whether the EMG mode has been manually selected or not. If the EMG mode has been manually selected at 404, the method can proceed to step 412, discussed in further detail below. Otherwise, the method proceeds to step 406.

After the initialization of the prosthetic arm prosthesis 100 at step 402 and, optionally, the determination at step 404 that auto-selection of mode is desired, the method can proceed to step 406. At step 406, sensor information for the prosthetic arm prosthesis 100 is received by controller 116. This sensor information can include, for example, signals from IMS 118, signals from EMG sensors 114, configuration/position information for joints in arm prosthesis 100 (e.g., powered elbow joint 108, wrist joint 112, and/or joints in prosthetic hand 110), or any combination thereof. Once the sensor information is received by controller 116 at step 406, the method proceeds to step 408. At step 408, the current motion, orientation, and configuration of arm prosthesis 100, and thus that of the residual limb by way of upper arm portion 102, with respect to the inertial reference frame, is computed.

Thereafter, the information obtained at step 408 for the arm prosthesis 100 and the residual limb is utilized at step 410 to auto-select a mode of operation for the arm prosthesis 100. As noted above, the arm prosthesis 100 can be operated in a coordinated control mode or a conventional EMG control mode based on the orientation of the arm prosthesis 100 and/or control signals being received (e.g., signals from EMG sensors 114). Further, as also noted above, the type of coordinated control or even the type of conventional EMG control to be provided for arm prosthesis 100 can also vary based on the current motion, orientation, or the configuration of the arm prosthesis 100.

Once the control mode is auto-selected at step 408 (or a manual EMG control mode is determined at step 404), the control signals appropriate for the current control mode can be generated at step 412 and the prosthetic arm prosthesis 100 is operated. In an EMG control mode, the joints are operated conventionally, based on signals from EMG sensors 114. In a coordinated control mode, the control signals can be based solely on the current motion, orientation, and configuration of the arm prosthesis 100. However, as also discussed above, these control signals can also be based on a combination of the current motion, orientation, and configuration and the control signals provided by the user via EMG sensors 114. For example, as discussed above, EMG signals can be used to modulate or modify the motion in a particular mode.

Thereafter, steps 406, 408, 410, and 412 are repeated continuously. Optionally, after step 412, a determination can be made as to whether the current operation mode has changed. That is, whether the controller detects the user manually selecting going to the EMG control mode or the auto-select mode of operation. If there is no change, the method proceeds to repeat method 400 starting with step 406. Otherwise, the method proceeds to repeat method 400 starting with step 404.

Figure 5A:
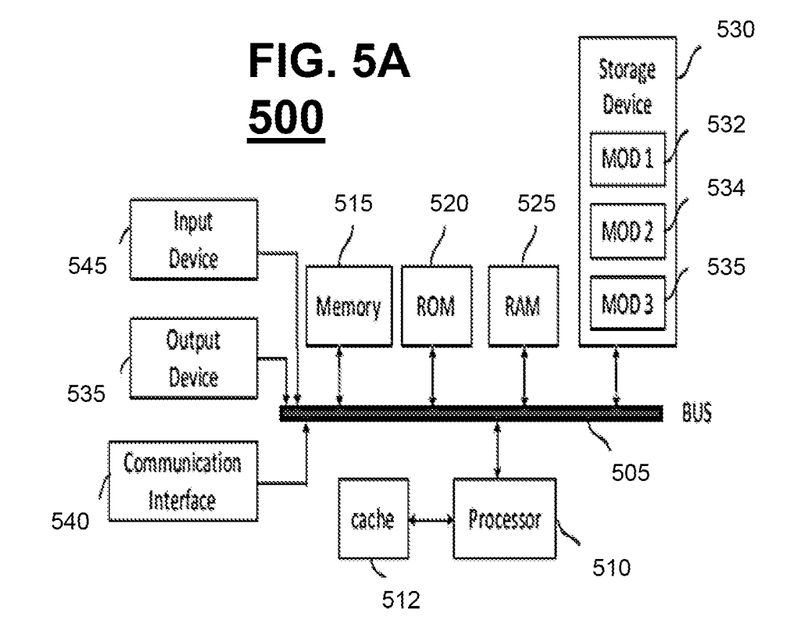
FIGS. 5A and 5B show a system embodiment suitable for implementing the control system of the present technology.
Figure 5B:
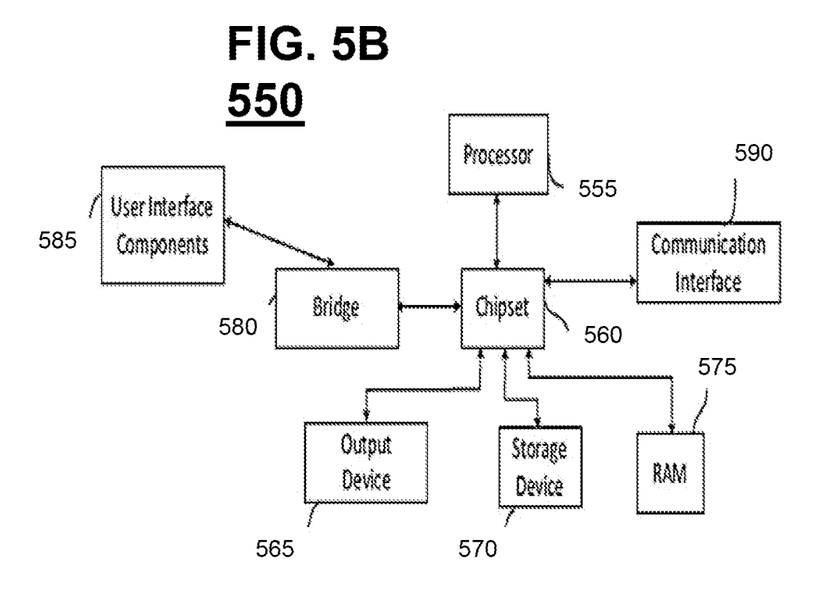

FIG. 5A, and FIG. 5B illustrate exemplary possible system embodiments for a controller for carrying out the various embodiments in accordance with the present technology. The more appropriate embodiment will be apparent to those of ordinary skill in the art when practicing the present technology. Persons of ordinary skill in the art will also readily appreciate that other system embodiments are possible.

FIG. 5A illustrates a conventional system bus computing system architecture 500 wherein the components of the system are in electrical communication with each other using a bus 505. Exemplary system 500 includes a processing unit (CPU or processor) 510 and a system bus 505 that couples various system components including the system memory 515, such as read only memory (ROM) 520 and random access memory (RAM) 525, to the processor 510. The system 500 can include a cache of high-speed memory connected directly with, in close proximity to, or integrated as part of the processor 510. The system 500 can copy data from the memory 515 and/or the storage device 530 to the cache 512 for quick access by the processor 510. In this way, the cache can provide a performance boost that avoids processor 510 delays while waiting for data. These and other modules can control or be configured to control the processor 510 to perform various actions. Other system memory 515 may be available for use as well. The memory 515 can include multiple different types of memory with different performance characteristics. The processor 510 can include any general purpose processor and a hardware module or software module, such as module 1 532, module 2 534, and module 3 536 stored in storage device 530, configured to control the processor 510 as well as a special-purpose processor where software instructions are incorporated into the actual processor design. The processor 510 may essentially be a completely self-contained computing system, containing multiple cores or processors, a bus, memory controller, cache, etc. A multi-core processor may be symmetric or asymmetric.

To enable user interaction with the computing device 500, an input device 545 can represent any number of input mechanisms, such as a microphone for speech, a touch-sensitive screen for gesture or graphical input, keyboard, mouse, motion input, speech and so forth. An output device 535 can also be one or more of a number of output mechanisms known to those of skill in the art. In some instances, multimodal systems can enable a user to provide multiple types of input to communicate with the computing device 500. The communications interface 540 can generally govern and manage the user input and system output. There is no restriction on operating on any particular hardware arrangement and therefore the basic features here may easily be substituted for improved hardware or firmware arrangements as they are developed.

Storage device 530 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 525, read only memory (ROM) 520, and hybrids thereof.

The storage device 530 can include software modules 532, 534, 536 for controlling the processor 510. Other hardware or software modules are contemplated. The storage device 530 can be connected to the system bus 505. In one aspect, a hardware module that performs a particular function can include the software component stored in a computer-readable medium in connection with the necessary hardware components, such as the processor 510, bus 505, display 535, and so forth, to carry out the function.

FIG. 5B illustrates a computer system 550 having a chipset architecture that can be used in executing the described method and generating and displaying a graphical user interface (GUI). Computer system 550 is an example of computer hardware, software, and firmware that can be used to implement the disclosed technology. System 550 can include a processor 555, representative of any number of physically and/or logically distinct resources capable of executing software, firmware, and hardware configured to perform identified computations. Processor 555 can communicate with a chipset 560 that can control input to and output from processor 555. In this example, chipset 560 outputs information to output 565, such as a display, and can read and write information to storage device 570, which can include magnetic media, and solid state media, for example. Chipset 560 can also read data from and write data to RAM 575. A bridge 580 for interfacing with a variety of user interface components 585 can be provided for interfacing with chipset 560. Such user interface components 585 can include a keyboard, a microphone, touch detection and processing circuitry, a pointing device, such as a mouse, and so on. In general, inputs to system 550 can come from any of a variety of sources, machine generated and/or human generated.

Chipset 560 can also interface with one or more communication interfaces 590 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 555 analyzing data stored in storage 570 or 575. Further, the machine can receive inputs from a user via user interface components 585 and execute appropriate functions, such as browsing functions by interpreting these inputs using processor 555.

It can be appreciated that exemplary systems 500 and 550 can have more than one processor 510 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. Also, the terms "about", "substantially", "essentially", and "approximately", as used herein with respect to a stated value, property, or condition are intend to indicate being within 20% or less of the stated value, property, or condition unless otherwise specified above. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method for the control of an arm prosthesis having at least one powered joint and at least one inertial measurement sensor (IMS), characterized in that the method comprising:
    determining a motion of the arm prosthesis relative to the inertial reference frame based at least on an output of the IMS;
    generating control signals for the at least one powered joint based on the motion and the orientation of the prosthetic arm
    wherein the at least one powered joint comprises a powered elbow joint, wherein the IMS measures the motion of an upper arm portion of the arm prosthesis, and wherein the generating the control signals comprises controlling an angular movement of the powered elbow joint based on the motion of the upper arm portion; and
    wherein the generating of control signals comprises:
    determining a motion of the powered elbow joint with respect to a body of a user based on the orientation and motion of the arm prosthesis with respect to the body;
    configuring the control signals to move the powered elbow joint in extension when the powered elbow joint is moving away from the body; and
    configuring the control signals to move the powered elbow joint in flexion when the powered elbow joint is moving closer toward the body.

2. The method of claim 1, wherein determining the motion of the powered elbow joint with respect to the body comprises determining a change in at least one of a radial distance from the powered elbow joint to at least one of a centerline of the body or a distance of the powered elbow joint from a preselected plane relative to the body.

3. The method of claim 1, wherein the generating of control signals comprises: determining a velocity vector for the powered elbow joint with respect to a body of a user in a direction orthogonal to both an axis of rotation of the powered elbow joint and a long axis of the upper arm portion based on the orientation and motion of the arm prosthesis with respect to the body.

4. The method of claim 1, wherein the generating of control signals comprises:
    determining an angular velocity of the upper arm portion with respect to the inertial reference frame; and
    configuring the control signals to move the powered elbow joint according to the angular velocity.

5. The method of claim 4, further comprising determining an angle of internal/external shoulder rotation.

6. The method of claim 1, wherein the generating of control signals further comprises:
    determining whether the upper arm portion is moving in a plane orthogonal to an axis of rotation of the powered elbow joint; and
    upon determining that the upper arm portion is moving in a plane orthogonal to the axis of the powered elbow joint, configuring the control signals to maintain an orientation of a forearm portion of the arm prosthesis invariant.

7. The method of claim 1, wherein the control signals also comprise electromyogram (EMG) signals, and wherein the generating of the control signals further comprises modulating an amount of motion of the at least one powered joint based on the EMG signals.

8. The method of claim 7, where a sustained co-contraction as indicated by the EMG signal attenuate the amount of motion based on a strength of the co-contraction.

9. The method of claim 1, further comprising:
    selecting a mode of operating the at least one powered joint based at least on the motion of the upper arm portion; and
    configuring the control signals based on the selected mode.

10. The method of claim 1, where the at least one powered joint is a powered wrist joint between a forearm portion and a hand portion of the prosthetic arm.

11. The method of claim 10, where the configuring of the control signals comprises configuring the control signals for the powered wrist joint to maintain an orientation of the hand portion invariant relative to the inertial reference frame.

12. A non-transitory computer-readable medium having stored thereon a computer program for controlling a prosthetic arm, characterized in that the computer program comprising a plurality of instructions for carrying out the method of claim 1.

13. A control system for a prosthetic arm comprising an upper arm portion, a forearm portion, a powered elbow joint, and an inertial measurement sensor, the control system comprising:
    a processor; and
    a non-transitory computer readable medium, characterized in that the computer readable medium having stored thereon a plurality of instructions for causing the processor to perform the steps of claim 1.

* * * * *